United States Patent
Satake et al.

(10) Patent No.: US 9,219,888 B2
(45) Date of Patent: Dec. 22, 2015

(54) IMAGE PICKUP UNIT AND ENDOSCOPE

(71) Applicant: OLYMPUS CORPORATION, Tokyo (JP)

(72) Inventors: Nau Satake, Yokohama (JP); Hiroyuki Motohara, Hachioji (JP); Junya Yamada, Kawasaki (JP); Takanori Sekido, Machida (JP); Mikio Nakamura, Nishitama-gun (JP)

(73) Assignee: OLYMPUS CORPORATION, Tokyo (JP)

( * ) Notice: Subject to any disclaimer, the term of this patent is extended or adjusted under 35 U.S.C. 154(b) by 332 days.

(21) Appl. No.: 13/954,144

(22) Filed: Jul. 30, 2013

(65) Prior Publication Data
US 2013/0314521 A1 Nov. 28, 2013

Related U.S. Application Data

(63) Continuation of application No. PCT/JP2011/077076, filed on Nov. 24, 2011.

(30) Foreign Application Priority Data

Mar. 8, 2011 (JP) ................................. 2011-050534

(51) Int. Cl.
| | |
|---|---|
| *H04N 7/18* | (2006.01) |
| *A61B 1/00* | (2006.01) |
| *G02B 23/24* | (2006.01) |
| *A61B 1/05* | (2006.01) |

(52) U.S. Cl.
CPC ............... *H04N 7/18* (2013.01); *A61B 1/0011* (2013.01); *A61B 1/00096* (2013.01); *A61B 1/051* (2013.01); *G02B 23/2423* (2013.01); *G02B 23/2484* (2013.01)

(58) Field of Classification Search
CPC ......................... G02B 23/2423; G02B 23/2484
USPC ........................................................... 600/101
See application file for complete search history.

(56) References Cited

U.S. PATENT DOCUMENTS

| | | | | |
|---|---|---|---|---|
| 4,741,327 A | * | 5/1988 | Yabe | 600/130 |
| 4,832,003 A | * | 5/1989 | Yabe | 600/109 |

(Continued)

FOREIGN PATENT DOCUMENTS

| | | |
|---|---|---|
| EP | 2 031 430 A2 | 3/2009 |
| JP | 63-259507 A | 10/1988 |

(Continued)

OTHER PUBLICATIONS

International Search Report dated Jan. 10, 2012 issued in PCT/JP2011/077076.

(Continued)

*Primary Examiner* — Andy Rao
*Assistant Examiner* — Tyler Edwards
(74) *Attorney, Agent, or Firm* — Scully, Scott, Murphy & Presser, PC

(57) ABSTRACT

An image pickup unit includes an image pickup device, an objective lens, and a prism that has a reflective surface. The image pickup unit includes: a projecting portion that is an area at which the image pickup device projects to the rear from the prism; a terminal portion provided on the projecting portion; a flexible printed wiring board that extends along the prism and the projecting portion; an image pickup device connection terminal portion formed on a face that faces the projecting portion of the flexible printed wiring board; and a cable connection terminal portion formed at an area that extends over the projecting portion of the flexible printed wiring board. The terminal portion and the image pickup device connection terminal portion are joined in an opposed state. An electronic component is mounted on a face on an opposite side to the reflective surface of the flexible printed wiring board.

4 Claims, 7 Drawing Sheets

(56) References Cited

U.S. PATENT DOCUMENTS

2009/0062616 A1*  3/2009  Nagamizu et al. ............ 600/173
2009/0296235 A1* 12/2009  Igarashi ....................... 359/720

FOREIGN PATENT DOCUMENTS

| JP | 09-173287 A | 7/1997 |
|---|---|---|
| JP | 11-352413 A | 12/1999 |
| JP | 2008-118568 A | 5/2008 |
| JP | 2009-058807 A | 3/2009 |
| JP | 2009-288682 A | 12/2009 |
| JP | 2010-268077 A | 11/2010 |

OTHER PUBLICATIONS

Extended Supplementary European Search Report dated Oct. 9, 2014 from related European Application No. 11 86 0522.9.

* cited by examiner

IMAGE PICKUP UNIT AND ENDOSCOPE

CROSS REFERENCE TO RELATED APPLICATION

This application is a continuation application of PCT/JP2011/077076 filed on Nov. 24, 2011 and claims benefit of Japanese Application No. 2011-050534 filed in Japan on Mar. 8, 2011, the entire contents of which are incorporated herein by this reference.

BACKGROUND OF THE INVENTION

1. Field of the Invention

The present invention relates to an image pickup unit including an image pickup device, an objective lens, and a prism having a reflective surface for bending an optical axis of the objective lens, and also to an endoscope.

2. Description of the Related Art

In medical fields or industrial fields, for example, in order to observe locations which are difficult to observe inside a body of a living organism or inside a structure or the like, an endoscope that includes an image pickup unit for picking up an optical image and that can be introduced into the living organism or the structure from outside is utilized to perform such observation.

An image pickup unit of an endoscope includes an objective lens that forms an object image, and an image pickup device that is commonly referred to as a CCD (charge coupled device) or a CMOS (complementary metal-oxide semiconductor) sensor or the like that is arranged on an image-forming surface of the objective lens.

For example, an image pickup unit disclosed in Japanese Patent Application Laid-Open Publication No. 11-352413 or Japanese Patent Application Laid-Open Publication No. 2009-58807 has a configuration in which a prism is arranged between an objective lens and an image pickup device, and an optical axis of the objective lens is bent by the prism. According to the image pickup unit disclosed in Japanese Patent Application Laid-Open Publication No. 11-352413 or Japanese Patent Application Laid-Open Publication No. 2009-58807, the prism is fixed inside a frame-shaped member.

An image pickup unit also includes a cable connection terminal portion to which an electrical cable is connected and an electronic component. For example, in the image pickup unit disclosed in Japanese Patent Application Laid-Open Publication No. 11-352413, a printed wiring board is provided on a rear face side of a reflective surface of the prism, and a cable connection terminal portion is formed on the printed wiring board. Further, in the image pickup unit disclosed in Japanese Patent Application Laid-Open Publication No. 2009-58807, a printed wiring board is extended to outside of a frame-shaped member that houses a prism and an image pickup device, and an electronic component is mounted thereon.

SUMMARY OF THE INVENTION

An image pickup unit according to the present invention includes an image pickup device, an objective lens that forms an object image on a light receiving portion of the image pickup device, and a prism having a reflective surface for bending an optical axis of the objective lens between the objective lens and the light receiving portion, in which a face on which the light receiving portion of the image pickup device is provided and an exit face of the prism are joined; the image pickup unit including: a holding frame that is a frame-shaped member that surrounds the optical axis of the objective lens, and holds the prism therein; a projecting portion that is an area at which the image pickup device projects in an opposite direction to the objective lens from the prism; a terminal portion for performing electrical inputting and outputting to and from the image pickup device, that is provided on a face on a same side as a face on which the light receiving portion is provided of the projecting portion; a flexible printed wiring board that extends over a rear face of the reflective surface of the prism and over a face on which the terminal portion is provided of the projecting portion; an image pickup device connection terminal portion that is formed on a face that faces the projecting portion of the flexible printed wiring board; and a cable connection terminal portion that is formed on a face on an opposite side to the face on which the image pickup device connection terminal portion is provided at an area that extends over the projecting portion of the flexible printed wiring board, and to which an electrical cable for electrically connecting the image pickup device to an external apparatus is connected; in which the terminal portion and the image pickup device connection terminal portion are joined in an opposed state, and an electronic component is mounted on a face on an opposite side to the reflective surface at an area that extends over the rear face of the reflective surface of the flexible printed wiring board. Further, an endoscope according to the present invention includes the image pickup unit.

DETAILED DESCRIPTION OF THE PREFERRED EMBODIMENTS

Preferred embodiments of the present invention are described hereunder with reference to the accompanying drawings. Note that the components in the accompanying drawings referred to in the following description are each displayed in a different contraction scale so as to be shown in a size that is recognizable in the accompanying drawings. Further, the present invention is not limited to only the quantity of components, the shapes of components, the ratios between the sizes of components, and the relative positional relationship between the respective components described in the accompanying drawings.

First Embodiment

Figure 1:
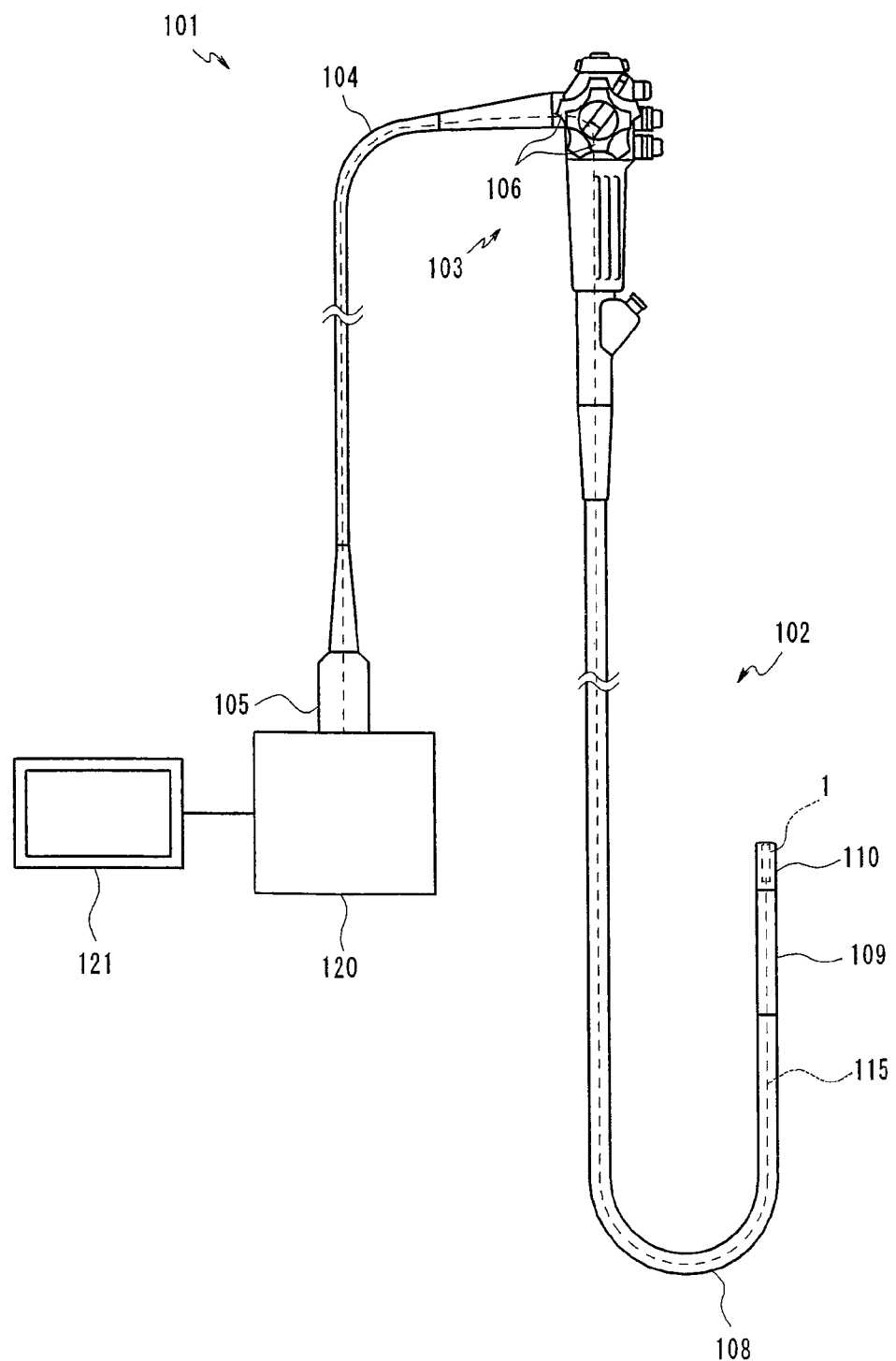
FIG. 1 is a view that illustrates the configuration of an endoscope according to a first embodiment.

One example of an embodiment of the present invention is described hereunder. First, an example of the configuration of an endoscope 101 that includes an image pickup unit 1 according to the present invention will be described referring to FIG. 1. The endoscope 101 of the present embodiment has a configuration that can be introduced into the inside of a subject such as a human body and optically picks up an image of a predetermined site to be observed inside the subject. Note that a subject into which the endoscope 101 is introduced is not limited to a human body, and may be another living organism or may be a man-made object such as a machine or a building structure or the like.

The endoscope 101 mainly includes an insertion portion 102 that is introduced into the inside of a subject, an operation portion 103 that is positioned at a proximal end of the insertion portion 102, and a universal cord 104 that extends from a side portion of the operation portion 103.

The insertion portion 102 includes a distal end portion 110 that is arranged at a distal end, a bendable bending portion 109 that is arranged on a proximal end side of the distal end portion 110, and a flexible tube portion 108 that has flexibility and is arranged on a proximal end side of the bending portion 109 and is connected to a distal end side of the operation portion 103. The aforementioned portions are connected in series. Note that the endoscope 101 may be of a form referred to as a so-called "rigid endoscope" that does not include an area that has flexibility in the insertion portion.

Although described in further detail later, the image pickup unit 1 and an illuminating light exit portion 113 (not shown in FIG. 1) are provided in the distal end portion 110. An angle operation knob 106 for operating bending of the bending portion 109 is provided in the operation portion 103.

An endoscope connector 105 that is connected to an external apparatus 120 is provided at a proximal end portion of the universal cord 104. The external apparatus 120 to which the endoscope connector 105 is connected is equipped with, for example, a light source portion, an image processing portion, and an image display portion 121.

The endoscope 101 also includes an electrical cable 115 and a fiber optic bundle 114 (not shown in FIG. 1) that are inserted through the inside of the universal cord 104, the operation portion 103 and the insertion portion 102.

The electrical cable 115 is configured so as to electrically connect the connector portion 105 and the image pickup unit 1. By connecting the connector portion 105 to the external apparatus 120, the image pickup unit 1 is electrically connected to an image processing portion of the external apparatus 120 through the electrical cable 115.

The image processing portion has a configuration that generates a video signal based on an image pickup device output signal that is outputted from the image pickup unit 1, and outputs the video signal to the image display portion 121. That is, according to the present embodiment, an optical image that was picked up by the image pickup unit 1 is displayed as a video on the display portion 121. Note that a configuration may also be adopted in which part or all of the image processing portion and the image display portion 121 are arranged in the endoscope 101.

The fiber optic bundle 114 is configured to transmit light that has been emitted from the light source portion of the external apparatus 120 to the illuminating light exit portion 113 of the distal end portion 110. Note that a configuration may also be adopted in which the light source portion is arranged in the operation portion 103 or the distal end portion 110 of the endoscope 101.

Figure 2:
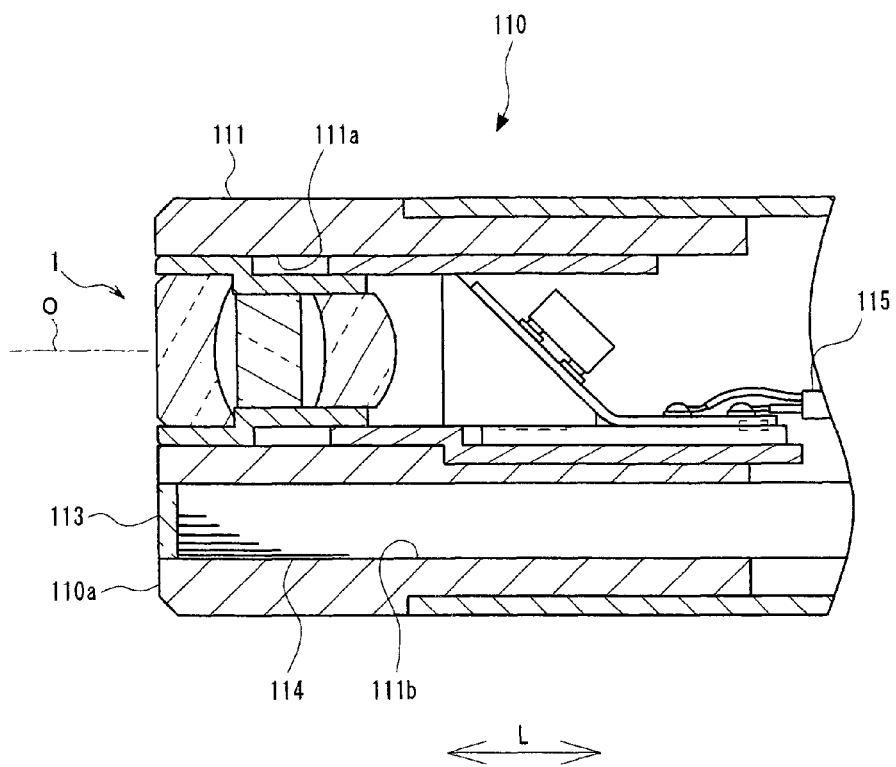
FIG. 2 is a view that illustrates the configuration of a distal end portion of the endoscope according to the first embodiment.

Next, the configuration of the distal end portion 110 is described. As shown in FIG. 2, the image pickup unit 1 and the illuminating light exit portion 113 are arranged in the distal end portion 110.

As one example according to the present embodiment, the image pickup unit 1 is arranged so as to pick up an image in a distal end direction beyond a distal end face of the distal end portion 110 along the longitudinal direction (insertion axis direction) of the insertion portion 102 that is indicated by an arrow L in FIG. 2. More specifically, the image pickup unit 1 is arranged so that an image-pickup optical axis O that passes through the center of the field of view is along the longitudinal direction of the insertion portion 102. Note that the image pickup unit 1 may also be arranged so that the image-pickup optical axis O forms a predetermined angle with respect to the longitudinal direction of the insertion portion 102.

The illuminating light exit portion 113 has a configuration that emits light that is incident from the fiber optic bundle 114 so as to illuminate an object of the image pickup unit 1. According to the present embodiment, the illuminating light exit portion 113 is configured so as to emit light in the distal end direction from the distal end face of the distal end portion 110 along the longitudinal direction of the insertion portion 102.

The image pickup unit 1 and the illuminating light exit portion 113 are held by a holding section 111 that is provided in the distal end portion 110. The holding section 111 is a rigid member that is exposed at a distal end face 110a of the distal end portion 110, and in which through-holes 111a and 111b are provided that are formed along the longitudinal direction of the insertion portion 102. The image pickup unit 1 and the illuminating light exit portion 113 are fixed by an adhesive or a method such as fastening with screws inside the through-holes 111a and 111b. The fiber optic bundle 114 is also inserted into the through-hole 111b from the proximal end side and fixed therein.

Figure 3:
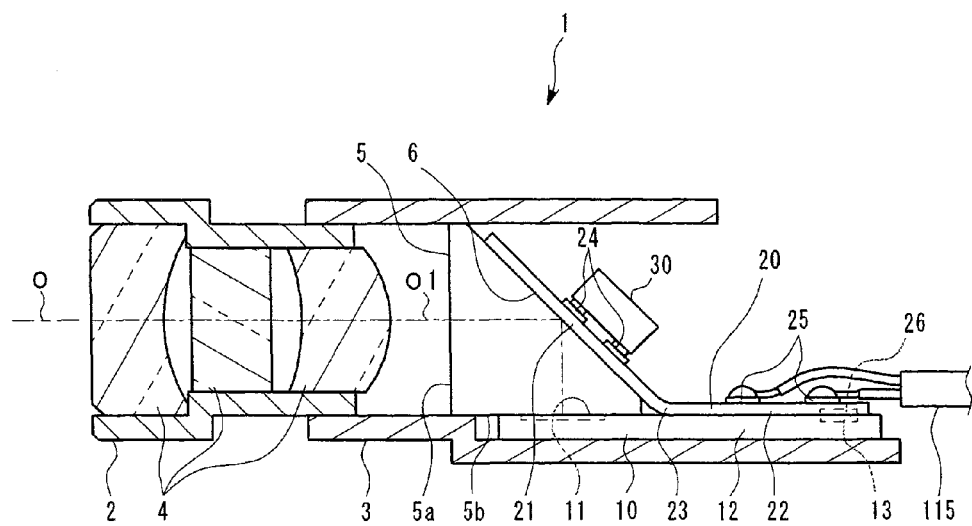
FIG. 3 is a view that illustrates the detailed configuration of an image pickup unit according to the first embodiment.

Next, the configuration of the image pickup unit 1 of the present embodiment will be described. As shown in FIG. 3, the image pickup unit 1 includes an objective lens 4, a prism 5, an image pickup device 10 and a flexible printed wiring board 20. These members that constitute the image pickup unit 1 are held by an approximately frame-shaped holding frame 3. According to the present embodiment, the holding frame 3 is a cylindrical member that surrounds the circumference of the image-pickup optical axis O.

Note that, hereunder, a direction towards the object from the image pickup unit 1 (leftward in FIG. 3) along the image-pickup optical axis O of the image pickup unit 1 is referred to as "front", and the opposite direction thereto is referred to as "rear".

The objective lens 4 is arranged inside a cylindrical lens barrel 2, and includes optical members such as one or a plurality of lenses for forming an object image on a light receiving portion 11 of the image pickup device 10 that is described later. The lens barrel 2 is fitted from the front into the holding frame 3, and is fixed by an adhesive or the like in a positioned state.

Although described in detail later, the prism 5, the image pickup device 10, and the flexible printed wiring board 20 are integrally joined to each other, and thereafter inserted from the rear into the holding frame 3 and fixed.

The prism 5 is arranged between the objective lens 4 and the light receiving portion 11 of the image pickup device 10.

The prism 5 has a reflective surface 6, and has a configuration that bends the optical axis by reflection at the reflective surface 6.

Hereunder, with respect to the optical axis of the image pickup unit 1, when particularly indicating only a part of the optical axis on an object side (front) of the prism 5, the optical axis on the object side (front) of the prism 5 is referred to as "optical axis O1 of the objective lens 4". The optical axis O1 of the objective lens 4 approximately coincides with the image-pickup optical axis O.

The prism 5 of the present embodiment is a so-called "rectangular prism", and includes an incident face 5a and an exit face 5b that are perpendicular to each other, and the reflective surface 6 that forms an angle of 45 degrees with respect to the incident face 5a and the exit face 5b. A reflective film is formed on the reflective surface 6. Note that, although not shown in the drawings, a thin film in a shape that functions as a diaphragm for preventing the occurrence of flares may be formed by an evaporation method or the like on the incident face 5a. The prism 5 is arranged so that the incident face 5a is approximately perpendicular to the optical axis O1 of the objective lens 4. Therefore, in the image pickup unit 1, the optical axis is bent at approximately a right angle.

The prism 5 is fitted from the rear into the holding frame 3, and is fixed by an adhesive or the like in a positioned state. That is, the holding frame 3 of the present embodiment has a hole portion that is formed in a direction along the optical axis O1 of the objective lens 4. The prism 5 is inserted from the rear into the hole portion of the holding frame 3 in a state in which the incident face 5a faces the front.

The image pickup device 10 is a component in which a plurality of elements that output an electrical signal at a predetermined timing in response to incident light are arrayed on the sheet-like light receiving portion 11. For example, an image pickup device of a type that is generally referred to as a CCD (charge coupled device) or a CMOS (complementary metal-oxide semiconductor) sensor, or of another type can be applied. As described above, the image pickup device 10 is arranged so that the light receiving portion 11 is positioned on an image-forming surface of the objective lens 4.

The image pickup device 10 is fixed to the prism 5 by joining the face on which the light receiving portion 11 is provided and the exit face 5b of the prism 5 by means of a transparent adhesive or the like. As a result of the light receiving portion 11 being bonded in a state facing the exit face 5b of the prism 5 in this manner, a luminous flux that is emitted from the objective lens 4 and reflected by the reflective surface 6 of the prism 5 is incident on the light receiving portion 11. According to the present embodiment, because the prism 5 is a rectangular prism, the light receiving portion 11 is approximately parallel with the optical axis O1 of the objective lens 4.

The image pickup device 10 has a projecting portion 12 that extends further to the rear than the prism 5 in a state in which the image pickup device 10 is fixed to the prism 5. At the projecting portion 12 of the image pickup device 10, a terminal portion 13 is provided on a face that is on the same side as the face on which the light receiving portion 11 is provided. The terminal portion 13 is a component for performing electrical inputting and outputting to and from the image pickup device 10.

Note that the image pickup device 10 of the present embodiment has a configuration in which, in addition to the light receiving portion 11 and the terminal portion 13, an electronic circuit included in the image pickup device 10 is formed on the same face of, for example, a silicon substrate using a so-called "semiconductor manufacturing process".

The flexible printed wiring board 20 is an electronic circuit board which is partially or entirely flexible. The flexible printed wiring board 20 is a component on which an electronic circuit is formed on a bendable film-like substrate that is made of a material that has an electrical insulating property.

The flexible printed wiring board 20 extends over the face on which the terminal portion 13 is provided (over the face on which the light receiving portion 11 is provided) of the projecting portion 12 of the image pickup device 10, and over the rear face of the reflective surface 6 of the prism 5. In other words, the flexible printed wiring board 20 extends along places that are exposed on the rear sides of the image pickup device 10 and the prism 5.

According to the present embodiment, the face on which the terminal portion 13 is provided of the image pickup device 10 is approximately parallel with the optical axis O1 of the objective lens 4, and the reflective surface 6 of the prism 5 is arranged so as to form an angle of approximately 45 degrees with respect to the optical axis O1 of the objective lens 4. Accordingly, the flexible printed wiring board 20 is arranged so as to be disposed over the face on which the terminal portion 13 of the projecting portion 12 is provided of the image pickup device 10 and over the rear face of the reflective surface 6 of the prism 5, in a state in which the flexible printed wiring board 20 is bent at an intermediate portion 23.

Hereunder, in a state in which the flexible printed wiring board 20 is fixed to the prism 5 and the image pickup device 10, an area that is further to the front side than the intermediate portion 23 of the flexible printed wiring board 20 is referred to as "front section 21", and an area that is further to the rear side than the intermediate portion 23 thereof is referred to as "rear section 22". In other words, the front section 21 is an area on the rear face of the reflective surface 6 of the prism 5, and the rear section 22 is an area on the face on which the terminal portion 13 of the projecting portion 12 is provided of the image pickup device 10.

The flexible printed wiring board 20 is fixed to at least one of the prism 5 and the image pickup device 10 by an adhesive or the like. Although a configuration in which the flexible printed wiring board 20 is fixed to at least one of the prism 5 and the image pickup device 10 is not particularly limited, as one example according to the present embodiment, the front section 21 of the flexible printed wiring board 20 is fixed to the prism 5 by an adhesive, a double-sided adhesive tape or the like. Note that a configuration may also be adopted in which the front section 21 and the rear section 22 are fixed by an adhesive, a double-sided adhesive tape or the like to the prism 5 and the image pickup device 10, respectively.

At the rear section 22 of the flexible printed wiring board 20, an image pickup device connection terminal portion 26 is provided at a position corresponding to the terminal portion 13 of the image pickup device 10 on a face that faces the projecting portion 12 of the image pickup device 10. The image pickup device connection terminal portion 26 constitutes a part of an electronic circuit formed on the flexible printed wiring board 20.

The image pickup device connection terminal portion 26 is joined with the terminal portion 13 in a state in which the image pickup device connection terminal portion 26 is opposed to the terminal portion 13 of the image pickup device 10 and in which an electrical connection is established between the image pickup device connection terminal portion 26 and the terminal portion 13. A method of joining the image pickup device connection terminal portion 26 and the terminal portion 13 is not particularly limited. Joining of the image pickup device connection terminal portion 26 and the terminal portion 13 may be performed by a known method such as, for example, soldering, eutectic bonding, diffusion joining, or use of an electrically conductive adhesive.

Further, at the rear section 22 of the flexible printed wiring board 20, a cable connection terminal portion 25 is provided on a face on an opposite side to the face that faces the image pickup device 10. The cable connection terminal portion 25 constitutes a part of an electronic circuit formed on the flexible printed wiring board 20.

The electrical cable 115 is connected to the cable connection terminal portion 25 by, for example, soldering. That is, the image pickup unit 1 is electrically connected to the electrical cable 115 through the cable connection terminal portion 25.

At the front section 21 of the flexible printed wiring board 20, an electronic component mounting portion 24 is provided on a face on an opposite side to the prism 5. The electronic component mounting portion 24 constitutes a part of an electronic circuit formed on the flexible printed wiring board 20. One or a plurality of electronic components 30 are mounted on the electronic component mounting portion 24 by, for example, soldering or use of an electrically conductive adhesive.

The kind of the electronic component 30 is not particularly limited, and is appropriately decided in accordance with the electronic circuit formed on the flexible printed wiring board 20. As one example according to the present embodiment, the electronic component 30 is a capacitor.

The order of assembling the image pickup unit 1 having the above described configuration will now be described. First, the prism 5 and the image pickup device 10 are fixed by an adhesive. In this process, the face on which the light receiving portion 11 is provided of the image pickup device 10 and the exit face 5b of the prism 5 are joined by means of a transparent adhesive.

Further, in a separate process to the process of fixing the image pickup device 10 to the prism 5, the electronic component 30 is mounted on the electronic component mounting portion 24 of the flexible printed wiring board 20.

Figure 4:
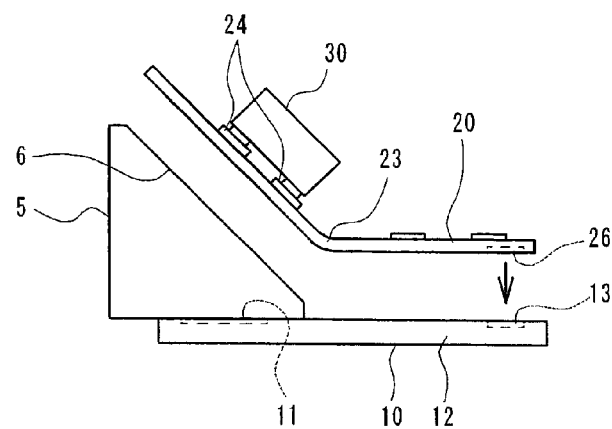
FIG. 4 is a view that illustrates a process of assembling the image pickup unit according to the first embodiment.

Next, as shown in FIG. 4, the flexible printed wiring board 20 is fixed to the prism 5 and the image pickup device 10, and the image pickup device connection terminal portion 26 and the terminal portion 13 are joined in an opposed state. In this process, the flexible printed wiring board 20 is bent at the intermediate portion 23 so that the flexible printed wiring board 20 is disposed over the face on which the terminal portion 13 of the projecting portion 12 is provided of the image pickup device 10, and over the rear face of the reflective surface 6 of the prism 5. Note that the order in which to perform the process of fixing the flexible printed wiring board 20 to the prism 5 and the image pickup device 10 and the process of joining the image pickup device connection terminal portion 26 and the terminal portion 13 is not particularly limited.

Figure 5:
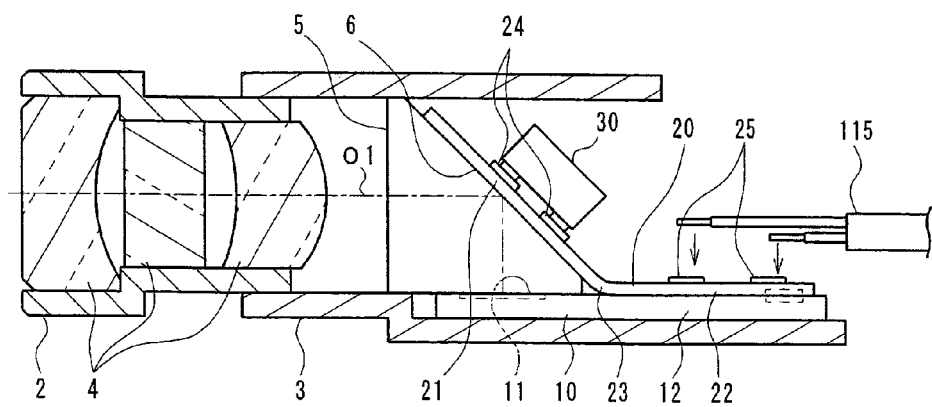
FIG. 5 is a view that illustrates a process of assembling the image pickup unit according to the first embodiment.

Next, the prism 5 in a state in which the flexible printed wiring board 20 and image pickup device 10 are fixed thereto is inserted into the holding frame 3 and fixed by an adhesive or the like. Thereafter, as shown in FIG. 5, the electrical cable 115 is connected by soldering to the cable connection terminal portion 25 of the flexible printed wiring board 20. Subsequently, the lens barrel 2 that holds lenses such as the objective lens 4 is positioned and fixed in the holding frame 3. Fixing of the lens barrel 2 to the holding frame 3 is performed while checking a video that is generated based on an image pickup device output signal that the image pickup device 10 outputs.

The image pickup unit 1 of the present embodiment that is described above includes the objective lens 4 that forms an object image on the light receiving portion 11 of the image pickup device 10, and the prism 5 that has the reflective surface 6 for bending the optical axis O1 of the objective lens 4, and has a configuration in which the face on which the light receiving portion 11 is provided of the image pickup device 10 and the exit face 5b of the prism 5 are joined. According to the present embodiment, the image pickup device 10 has the projecting portion 12 that projects further to the rear than the prism 5, and the terminal portion 13 for performing inputting and outputting to and from the image pickup device 10 is provided on a face that is on the same side as the face on which the light receiving portion 11 of the projecting portion 12 is provided.

In addition, the image pickup unit 1 of the present embodiment includes the flexible printed wiring board 20 that is bent so as to be disposed over the face on which the terminal portion 13 of the projecting portion 12 is provided of the image pickup device 10, and over the rear face of the reflective surface 6 of the prism 5.

The cable connection terminal portion 25 to which the electrical cable 115 is connected is provided on the rear section 22 of the flexible printed wiring board 20. The rear section 22 is an area along the upper part of the projecting portion 12 of the image pickup device 10.

In the present embodiment having the above configuration, since the rear section 22 on which the cable connection terminal portion 25 is provided extends towards the rear approximately parallel to the optical axis O1 of the objective lens 4, as described above using FIG. 5, work to connect the electrical cable 115 to the cable connection terminal portion 25 by soldering or the like can be performed with ease.

Further, in the present embodiment, the image pickup device 10 and the flexible printed wiring board 20 are electrically connected by joining the terminal portion 13 and the image pickup device connection terminal portion 26 that are formed on faces that are opposite to each other.

In addition, in the present embodiment, the electronic component 30 is mounted on the same flexible printed wiring board 20 as the image pickup device connection terminal portion 26 and the cable connection terminal portion 25. Consequently, an electrical connection between the electronic component 30, the image pickup device 10, and the cable connection terminal portion 25 is made only through the flexible printed wiring board 20.

Therefore, in comparison to the conventional case in which the image pickup device and the printed wiring board are electrically connected using, for example, wire bonding, in the case of the present embodiment an electrical connection between the image pickup device 10 and the flexible printed wiring board 20 can be realized by a simple and small-sized configuration, and work to make the electrical connection can be performed with ease.

Further, in the present embodiment, the electronic component 30 is arranged on the rear face side of the reflective surface 6 of the prism 5. That is, the electronic component 30 is arranged in an approximately triangular column-shaped space that is formed on the rear face side of the reflective surface 6 of the prism 5 inside the holding frame 3. By this configuration, in the image pickup unit 1 of the present embodiment, each member can be compactly disposed inside a smaller space than in the conventional technology, and the image pickup unit 1 can be reduced in size.

As described above, the image pickup unit 1 of the present embodiment has a simple and small-sized configuration, and can be easily assembled. Further, in the endoscope 101 that includes the image pickup unit 1, the size of the distal end portion 110 of the insertion portion 102 can be reduced.

Second Embodiment

A second embodiment of the present invention is described hereunder. In the present embodiment, the configuration of the flexible printed wiring board 20 of the image pickup unit 1 is different from the first embodiment. Hence, only differences with respect to the first embodiment are described hereunder, and components that are the same as in the first embodiment are denoted by the same reference numerals and a description thereof is omitted as appropriate.

Figure 6:
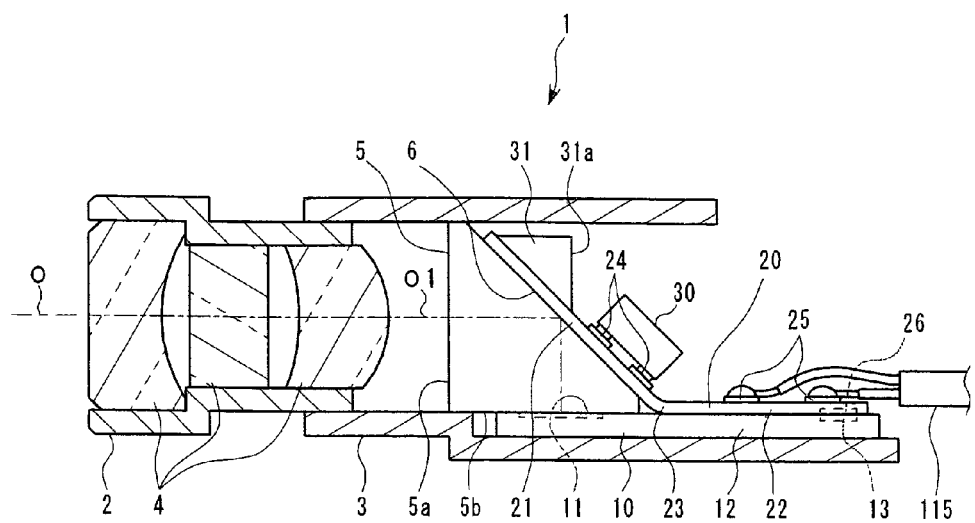
FIG. 6 is a view that illustrates the detailed configuration of an image pickup unit according to a second embodiment.

As shown in FIG. 6, the image pickup unit 1 of the present embodiment has a convex portion 31 on a face on an opposite side to the prism 5 of the front section 21 of the flexible printed wiring board 20. The convex portion 31 is a member that has a shape that protrudes from the flexible printed wiring board 20, and on which a flat portion 31a that is approximately perpendicular to the optical axis O1 of the objective lens 4 is formed. In other words, the convex portion 31 is a member that is fixed to the prism 5 on a rear face side of the reflective surface 6 of the prism 5. In addition, the convex portion 31 has the flat portion 31a that faces the rear side at a position that is more rearward than the prism 5. The flat portion 31a is approximately parallel with the incident face 5a of the prism 5.

As one example according to the present embodiment, the convex portion 31 has a triangular column-like shape that looks like a right-angled isosceles triangle when viewed along an axis that is perpendicular to the optical axis O1 of the objective lens 4 and is parallel to the reflective surface 6 of the prism 5 (viewing point in FIG. 6), and is fixed to the flexible printed wiring board 20 so that one face among two faces that meet at right angles is the flat portion 31a that is perpendicular to the optical axis O1 of the objective lens 4.

Note that the shape of the convex portion 31 is not limited to the shape in the present embodiment, and it is sufficient if the convex portion 31a has the flat portion 31a that is approximately perpendicular to the optical axis O1 of the objective lens 4. For example, the convex portion 31 may be a member in which a flat plate is bent in an approximately V shape.

A method of fixing the convex portion 31 to the flexible printed wiring board 20 is not particularly limited. For example, the convex portion 31 may be fixed to the flexible printed wiring board 20 by an adhesive, or for example, the convex portion 31 may be fixed to the flexible printed wiring board 20 by soldering.

As described above, the electronic component 30 and the convex portion 31 according to the present embodiment are arranged so as to protrude on the flexible printed wiring board 20 that is fixed to the rear face side of the reflective surface 6 of the approximately triangular column-shaped prism 5. That is, the electronic component 30 and the convex portion 31 are arranged within an approximately triangular column-shaped space that is formed on the rear face side (rear) of the reflective surface 6 of the prism 5.

Figure 7:
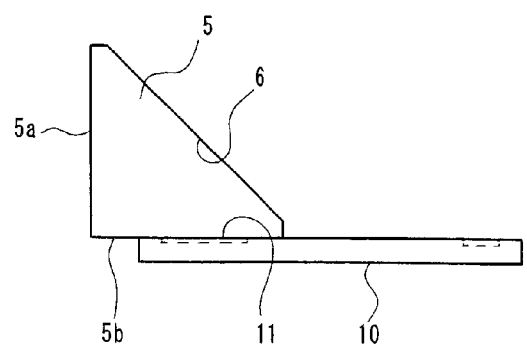
FIG. 7 is a view that illustrates a process of assembling the image pickup unit according to the second embodiment.

Next, the order of assembling the image pickup unit 1 of the present embodiment will be described. First, as shown in FIG. 7, the prism 5 and the image pickup device 10 are fixed by an adhesive. In this process, the face on which the light receiving portion 11 is provided of the image pickup device 10 and the exit face 5b of the prism 5 are joined by means of a transparent adhesive.

Figure 8:
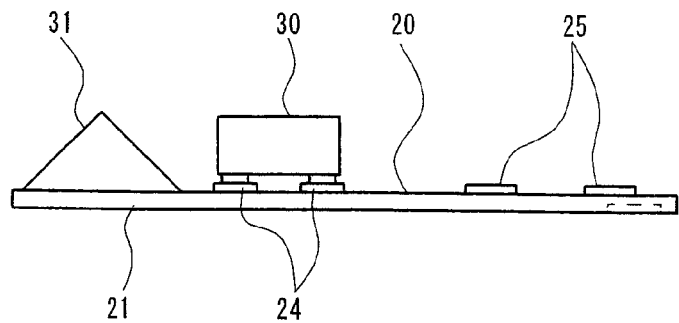
FIG. 8 is a view that illustrates a process of assembling the image pickup unit according to the second embodiment.

Further, in a separate process to the process of fixing the image pickup device 10 to the prism 5, as shown in FIG. 8, the electronic component 30 and the convex portion 31 are mounted onto the front section 21 of the flexible printed wiring board 20. That is, the electronic component 30 is mounted on the electronic component mounting portion 24, and the convex portion 31 is also fixed on the front section 21.

Note that the order of providing the electronic component 30 and the convex portion 31 on the flexible printed wiring board 20 is not particularly limited.

Figure 9:
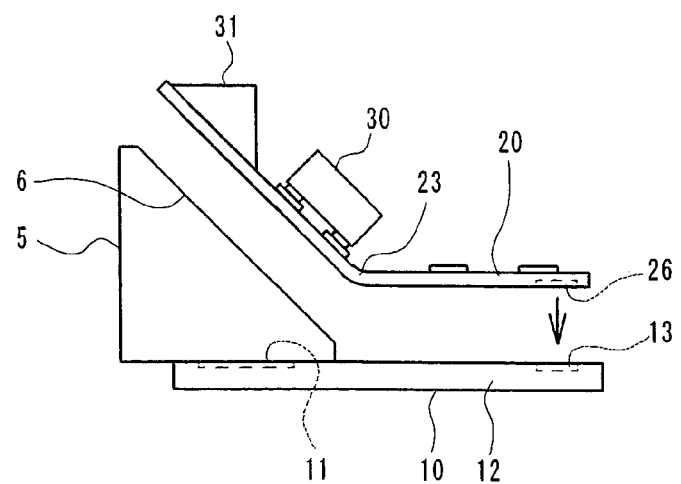
FIG. 9 is a view that illustrates a process of assembling the image pickup unit according to the second embodiment.

Next, as shown in FIG. 9, the flexible printed wiring board 20 is fixed to the prism 5 and the image pickup device 10, and the image pickup device connection terminal portion 26 and the terminal portion 13 are joined in an opposed state. In this process, the flexible printed wiring board 20 is bent at the intermediate portion 23 so that the flexible printed wiring board 20 is disposed over the face on which the terminal portion 13 of the projecting portion 12 of the image pickup device 10 is provided, and over the rear face of the reflective surface 6 of the prism 5. Note that the order in which to perform the process of fixing the flexible printed wiring board 20 to the prism 5 and the image pickup device 10 and the process of joining the image pickup device connection terminal portion 26 and the terminal portion 13 is not particularly limited.

Figure 10:
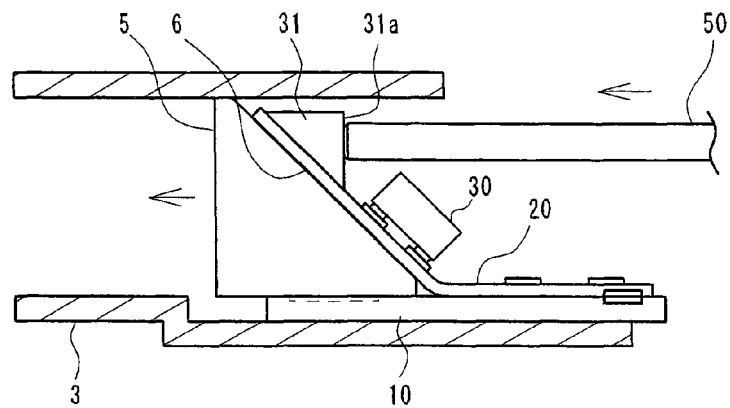
FIG. 10 is a view that illustrates a process of assembling the image pickup unit according to the second embodiment.

Next, as shown in FIG. 10, the prism 5 in a state in which the flexible printed wiring board 20 and image pickup device 10 are fixed thereto is inserted into the holding frame 3 and fixed by an adhesive or the like. In this process, the prism 5 is inserted into the holding frame 3 from the rear side of the holding frame 3. Work to insert the prism 5 into the holding frame 3 is performed by pressing the flat portion 31a of the convex portion 31 using a rod-shaped pressing member 50.

Figure 11:
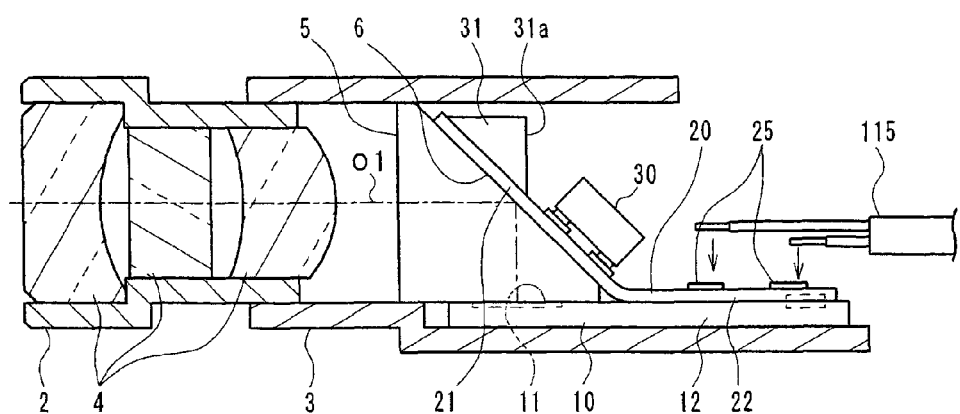
FIG. 11 is a view that illustrates a process of assembling the image pickup unit according to the second embodiment.

Next, as shown in FIG. 11, the electrical cable 115 is connected by soldering to the cable connection terminal portion 25 of the flexible printed wiring board 20. Subsequently, the lens barrel 2 that holds lenses such as the objective lens 4 is positioned and fixed in the holding frame 3. Fixing of the lens barrel 2 to the holding frame 3 is performed while checking a video that is generated based on an image pickup device output signal that the image pickup device 10 outputs.

The image pickup unit 1 of the present embodiment that is described above includes the convex portion 31. The convex portion 31 is fixed to the flexible printed wiring board 20, and the flexible printed wiring board 20 is fixed to the prism 5. The convex portion 31 is arranged inside an approximately triangular column-shaped space that is formed on the rear face side of the reflective surface 6 of the prism 5. The convex portion 31 has the flat portion 31a that is approximately perpendicular to the optical axis O1 of the objective lens 4, and faces the rear side at a position that is more rearward than the prism 5.

Consequently, according to the present embodiment, by using the pressing member 50 to apply a force to the flat portion 31a in a direction that is approximately perpendicular to the flat portion 31a, a force can be applied indirectly and easily to the prism 5 in the direction of inserting the prism 5 into the holding frame 3.

For example, in a conventional image pickup unit in which the convex portion 31 is not provided, when inserting the prism into the holding frame it has been necessary to directly contact the prism to press in the prism. According to this conventional image pickup unit, there is the risk that damage such as chipping of the prism or removal of a coating will be caused during the assembly work. In particular, in a case where the reflective surface is pressed when inserting the prism into the holding frame, because the reflective surface inclines with respect to the pressing direction, a force that tilts the prism arises at the time of insertion, and damage to the prism is more liable to occur.

With respect to this problem, according to the image pickup unit 1 of the present embodiment, by pressing the flat portion 31a of the convex portion 31 it is possible to insert the prism 5 into the holding frame 3 without contacting the prism 5, and hence the occurrence of damage to the prism 5 during the assembly work can be prevented.

In addition, the flat portion 31a of the convex portion 31 is approximately perpendicular to the optical axis O1 of the objective lens. That is, the flat portion 31a is perpendicular to the direction of inserting the prism 5 into the holding frame 3. Consequently, a force that tilts the prism 5 does not arise when inserting the prism 5 into the holding frame 3, and thus the occurrence of damage to the prism 5 during the assembly work can be prevented.

As described above, the image pickup unit 1 of the present embodiment prevents damage to the prism 5 at the time of assembly, and can be assembled with ease.

Note that since the image pickup unit 1 of the present embodiment differs from the first embodiment only with respect to the fact the present embodiment includes the convex portion 31, the advantages that the image pickup unit 1 has a simple and small-sized configuration and that assembly thereof can be performed with ease are the same as in the first embodiment.

Third Embodiment

A third embodiment of the present invention is described hereunder. The only difference between the present embodiment and the configuration of the second embodiment is the configuration of the convex portion 31 of the image pickup unit 1. Hence, only differences with respect to the second embodiment are described hereunder, and components that are the same as in the second embodiment are denoted by the same reference numerals and a description thereof is omitted as appropriate.

Figure 12:
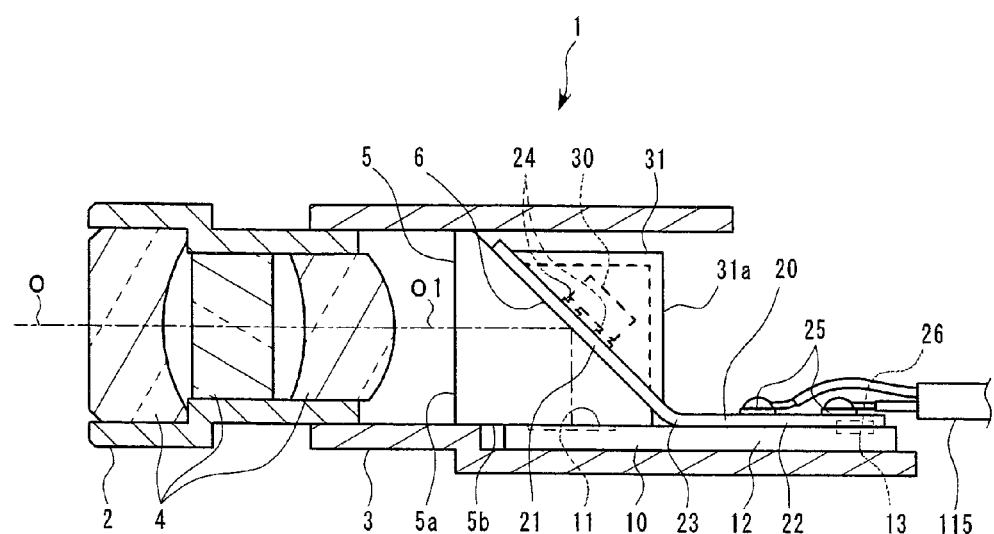
FIG. 12 is a view that illustrates the detailed configuration of an image pickup unit according to a third embodiment.

As shown in FIG. 12, according to the present embodiment the convex portion 31 is provided so as to cover the electronic component 30. The convex portion 31, for example, is a shell-like member that is made of synthetic resin that covers the upper part of the face on which the electronic component 30 is mounted of the front section 21 of the flexible printed wiring board 20. Similarly to the first embodiment, the convex portion 31 includes the flat portion 31a that is approximately perpendicular to the optical axis O1 of the objective lens 4.

The image pickup unit 1 of the present embodiment has the same advantages as in the first embodiment, and can also protect the electronic component 30 by means of the convex portion 31. For example, when assembling the image pickup unit 1, it is possible to prevent damage to the electronic component 30 caused by a tool or a finger of a worker or the like contacting the electronic component 30, and also prevent a decline in the connection strength between the electronic component 30 and the electronic component mounting portion 24.

Note that the convex portion 31 may also be a structure that is partially or entirely formed of an electrically conductive material. For example, the convex portion 31 can be configured as an electromagnetic shield by providing a metallic thin film on the surface of the convex portion 31 and electrically connecting the metallic thin film to a ground potential of the flexible printed wiring board 20.

A configuration may also be adopted in which resin is filled inside the convex portion 31 to seal the electronic component 30. By sealing the electronic component 30 using resin in this manner, the connection strength between the electronic component 30 and the electronic component mounting portion 24 can be improved.

Note that the present invention is not limited to the above described embodiments, but may be suitably changed without departing from the spirit or concept of the invention readable from the appended claims and the entire specification, and an image pickup unit and an endoscope with such changes are also included in the technical scope of the present invention.

What is claimed is:

1. An image pickup unit that includes an image pickup device, an objective lens that forms an object image on a light receiving portion of the image pickup device, and a prism having a reflective surface for bending an optical axis of the objective lens between the objective lens and the light receiving portion, in which a face on which the light receiving portion of the image pickup device is provided and an exit face of the prism are joined, the image pickup unit comprising:
a holding frame that is a frame-shaped member that surrounds the optical axis of the objective lens, and holds the prism therein;
a projecting portion that is an area at which the image pickup device projects in an opposite direction to the objective lens from the prism;
a terminal portion for performing electrical inputting and outputting to and from the image pickup device, which is provided on a face on a same side as a face on which the light receiving portion is provided of the projecting portion;
a flexible printed wiring board that extends over a rear face of the reflective surface of the prism and over a face on which the terminal portion is provided of the projecting portion;
an image pickup device connection terminal portion that is formed on a face that faces the projecting portion of the flexible printed wiring board; and
a cable connection terminal portion that is formed on a face on an opposite side to the face on which the image pickup device connection terminal portion is provided at an area that extends over the projecting portion of the flexible printed wiring board, and to which an electrical cable for electrically connecting the image pickup device to an external apparatus is connected;
wherein:
the terminal portion and the image pickup device connection terminal portion are joined in an opposed state; and
an electronic component is mounted on a face on an opposite side to the reflective surface at an area that extends over the rear face of the reflective surface of the flexible printed wiring board.

2. The image pickup unit according to claim 1, wherein:
a convex portion having a flat portion that is perpendicular to the optical axis of the objective lens is provided on the face on the opposite side to the reflective surface at the area that extends over the rear face of the reflective surface of the flexible printed wiring board; and
in a state in which the image pickup device is joined to the prism, the prism is inserted into the holding frame in a manner that takes an incident face thereof as a front side.

3. The image pickup unit according to claim 2, wherein the convex portion is provided so as to cover the electronic component.

4. An endoscope comprising an image pickup unit according to any one of claims 1 to 3.

* * * * *